United States Patent
Aspenberg et al.

(10) Patent No.: US 7,163,690 B2
(45) Date of Patent: Jan. 16, 2007

(54) BISPHOSPHONATE COATED IMPLANT DEVICE AND METHOD THEREFOR

(75) Inventors: Per Vilhelm Aspenberg, Linkoping (SE); Pentti Olavi Tengvall, Linkoping (SE)

(73) Assignee: Optovent AB, Linkoping (SE)

( * ) Notice: Subject to any disclaimer, the term of this patent is extended or adjusted under 35 U.S.C. 154(b) by 49 days.

(21) Appl. No.: 10/534,666

(22) PCT Filed: Jul. 1, 2004

(86) PCT No.: PCT/SE2004/001082

§ 371 (c)(1),
(2), (4) Date: May 11, 2005

(87) PCT Pub. No.: WO2005/018699

PCT Pub. Date: Mar. 3, 2005

(65) Prior Publication Data

US 2006/0003917 A1    Jan. 5, 2006

Related U.S. Application Data

(60) Provisional application No. 60/481,274, filed on Aug. 21, 2003.

(51) Int. Cl.
*A61F 2/00* (2006.01)
*A61F 2/02* (2006.01)
*A61K 9/28* (2006.01)

(52) U.S. Cl. .................... 424/423; 427/2.14; 623/11.11

(58) Field of Classification Search .................... None
See application file for complete search history.

(56) References Cited

OTHER PUBLICATIONS

Yoshinari et al. Immobilization of bisphosphonates on surface modified titanium. Biomaterials, 2001, vol. 22, p. 709-715.*
Kajiwara et al. The bisphosphonate pamidronate on the surface of titanium stimulates bone formation around tibial implants in rats. Biomaterials, 2005, vol. 26, p. 581-587.*
Tengvali et al. Surface immobilized bisphosphonate improves stainless-steel screw fixation in rats. Biomaterials, 2004, vol. 25, p. 2133-2138.*

* cited by examiner

*Primary Examiner*—Sikarl A. Witherspoon
(74) *Attorney, Agent, or Firm*—Bacon & Thomas PLLC

(57) ABSTRACT

The method of the present invention is for coating an implant device. The implant device is coated with a protein film, such as fibrinogen. A first bisphosphonate substance, such as pamidronate, is immobilized to the protein film. A second bisphosphonate substance, such ibandronate, is adsorbed to the first bisphosphonate wherein the first bisphosphonate is different from the second bisphosphonate.

10 Claims, 2 Drawing Sheets

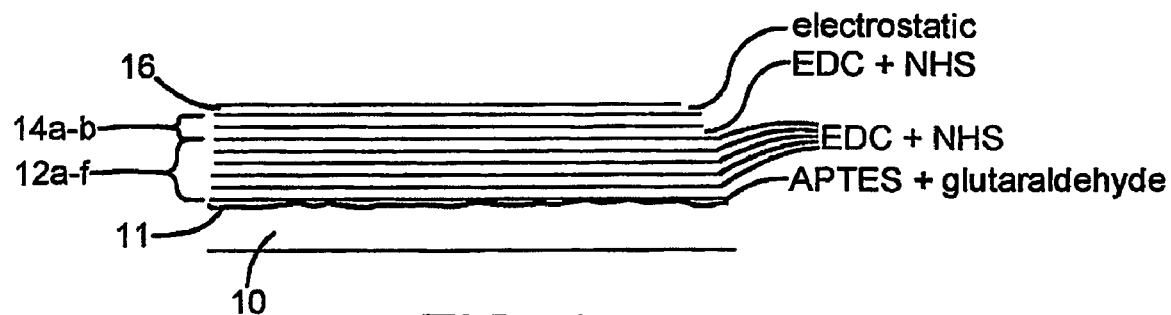
FIG. 1
FIG. 2
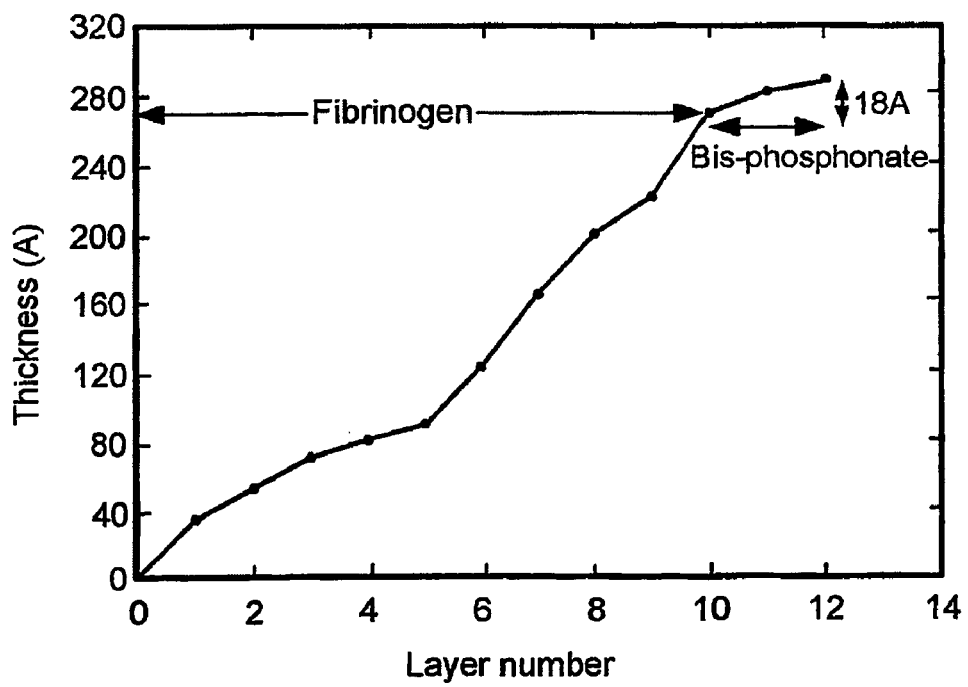

FIG. 3

Bisphosphonate immobilized to stainless steel - Pull-out. Stiffness and Energy until removal data Biomechanical data

| | | | | | Percent Increase by Bisphosphonate | | | |
| | | | | | 95 % CI | | | |
| Treatment | | n | m | sd | min | mean | max | p |
| --- | --- | --- | --- | --- | --- | --- | --- | --- |
| Force at Failure (N) | Control | 8 | 46 | 9 | 15 | 28 | 42 | 0.0009 |
| | Bisphosphonate | 8 | 60 | 3 | | | | |
| Stiffness (N/mm) | Control | 8 | 68 | 13 | -29 | -8 | 13 | 0.45 |
| | Bisphosphonate | 8 | 62 | 17 | | | | |
| Energy (Nmm) | Control | 8 | 15 | 5 | 49 | 90 | 132 | 0.0008 |
| | Bisphosphonate | 8 | 29 | 8 | | | | |

BISPHOSPHONATE COATED IMPLANT DEVICE AND METHOD THEREFOR

PRIOR APPLICATION

This application is a U.S. national phase application based on International Application No. PCT/SE2004/001082, filed 1 Jul. 2004, claiming priority from U.S. Provisional Patent Application No. 60/481,274, filed 21 Aug. 2003.

TECHNICAL FIELD

The present invention relates to a bisphosphonate coated implant device intended for use in humans and a method therefor.

BACKGROUND OF THE INVENTION

Live human bone adjacent to implants undergo simultaneous bone resorption and new bone formation. In an analogous manner, soft tissue around implants becomes remodelled after the initial wound healing period.

In bone, the above process results in adaptation of bone structure to functional demands and loading profile on the bone. At a normal bone fracture site, the dynamic interactions between bone resorption and formation ensure a healthy regeneration of the bone. In certain pathological conditions, such as loosening of orthopaedic joint prostheses, malignancy, and osteoporosis, bone resorption exceeds bone deposition. However, resorption may occur at an accelerated rate when orthopaedic implants are in contact with bone. This leads to both impaired early fixation and integration of the implant and early or late net bone loss at the site of implantation.

In soft tissue, a prolonged inflammation is more often observed around implants than around sham sites. This may be manifested as a delayed presence of inflammatory cells, such as macrophages and monocytes, as observed by e.g. immunohistochemical methods. The sustained inflammatory process is believed to result in a fibrous encapsulation of soft tissue implants.

Hydroxyapatite (HA) and tricalcium phosphate (TCP) coatings are widely used to improve the fixation of implants to bone for periods of a few weeks up to several months. However, HA and TCP coatings are expensive to prepare and diverging biological behavior has been reported. Also, HA and TCM coatings are often inadequate for long-term use. For certain applications, the currently available coated implants are not adequate and sometimes fail e.g. due to cracking after years of use.

The bone repair time around metallic implants may be in the range of months and is often described in terms of bone in-growth into threads, pores, holes and asperities. For certain applications, the implant can or should not be allowed to carry load until this process has lead to a sufficient surface/tissue binding strength. Such unloading is not always possible, and it is desirable to shorten the unloading time period.

Furthermore, some implants create a possibility for bacteria from the adjacent skin or mucous membrane to enter the interface between the implant and the surrounding tissue. In the case of so called external fixation devices, used in fracture treatment, this often leads to bone resorption and the device loosens within months. As already mentioned, conventional implants also have a tendency to cause prolonged inflammation and other undesirable tissue reactions especially in soft tissues.

SUMMARY OF THE INVENTION

The method and the bisphosphonate coated implant of the present invention provide a solution to the above-outlined problems. More particularly, the method of the present invention is for coating an implant device. The implant device is coated with a multi-layer of proteins, such as fibrinogen. A bisphosphonate substance, such as pamidronate, that has a chemically reactive group, such as an amino group, is covalently immobilized onto the protein film. A chemically non-reactive bisphosphonate substance, such as ibandronate, is adsorbed onto the first bisphosphonate substance wherein the two substances are different.

BRIEF DESCRIPTION OF THE DRAWINGS

FIG. 1 is a schematic cross-sectional view of the coated implant device of the present invention;

FIG. 2 is a schematic illustration of the thickness of the coating relative to the number of protein layers; and FIG. 3 is a table showing the improved mechanical properties of the implant device that has been coated according to the method of the present invention.

DETAILED DESCRIPTION

With reference to FIG. 1, a bisphosphonate coated implant device 10, preferably, has an etched surface 11 and several types of coating layers including a suitable protein layer 12, a first bisphosphonate layer 14 chemically bound to the layer 12 and a second bisphosphonate layer 16 disposed on top of and integrated with the first bisphosphonate layer 14. One important feature of the present invention is that the first bisphosphonate layer 14 is strongly bound while the second layer 16 is loosely bound and can quickly be released. This is important for the device-tissue interaction during the first couple of days after the implant device 10 has been inserted. The strongly bound first bisphosphonate layer 14 is slowly released over time to improve the long-term use of the implant device 10.

The implant device 10 may be any suitable material such as stainless steel, titanium, or any other non-metal material that provides sufficient support. The mechanical properties of stainless steel are often preferred due to a very high strength. The implant may be any device, for example a coated or uncoated metallic screw or a polymeric pad. As an illustrative example, the implant device 10 is made of stainless steel. Preferably, the surface 11 of the implant device 10 is etched or surface roughened. The surface topology of the implant device 10, particularly in terms of its roughness and porosity, may in itself affect tissue healing and implant success. Other surface treatment methods such as calcium mineral coating could also be used.

Preferably, the device 10 is first etched in an acid such as hydrofluoric acid (HF) or nitric acid, and then washed in hydrogen peroxide solution. The hydrogen peroxide provides a milder etching compared to hydrofluoric acid.

The protein layer 12 may be any suitable protein, such as immobilized and cross-linked fibrinogen, that is used to coat the surface 11. Preferably, a plurality of layers is used. For instance, a silane substance may be used to bind proteins onto the metal oxide (MOH$^-$) of the metallic device 10. A strong covalent ether binding may, by use of silane, be formed between the metal device and the first protein layer. More particularly, via covalent attachment of amino propyl triethoxy silane (APTES) to hydroxyl groups of the metal surface 11 a first fibrinogen layer 12a may be immobilized onto the stainless steel surface 11. It is also possible to replace APTES with some other substance that has an amino, carboxyl, SH or any other suitable chemical group. Amino groups of the APTES also react with aldehyde groups at one end of an aldehyde-based substance, such as glutardialdehyde. Glutardidehyde has a second aldehyde group that may be chemically bound to the amine terminal of the first protein layer 12a.

It would be possible to chemically bind the first bisphosphonate layer 14 directly to the aldehyde groups of the glutaraldehyde. However, the thickness of the single layer 14 may then be limited to about 5–6 Ångstroms. It is often desirable to bind more bisphosphonate than just one layer.

Further, a free carboxyl terminal of the first protein layer 12a is activated by a carbodiimide, such as ethyl-dimethyl-aminopropylcarbodiimide (EDC), and hydroxy-succinimide (NHS) to attract and by peptide bond formation capture more protein so as to form a second protein layer 12b. The EDC activates the carboxyl groups, of the first protein layer, so that amino groups of the protein in solution may be chemically bound thereto. By repetition of the EDC/NHS activation procedure, a plurality of protein layers may be immobilized and cross-linked. The total thickness of the protein layer 12 may be increased by increasing the number of layers. For example, ten layers of fibrinogen may be about 280 Ångstroms thick, as shown in FIG. 2. By cross-linking many layers of fibrinogen, and thus the number of reactive groups, to the device 10, it is possible to add an amount of the first bisphosphonate corresponding to two layers 14a–b (10–12 Ångstroms) and one layer of the second bisphosphonate 16 (6–7 Ångstroms). The total bisphosphonate layer may thus be about 18 Ångstroms. It is to be understood that the bisphosphonate layers are not only disposed on top of the protein layer 12f but are also mixed into the network of the layers 12a–e. The second bisphosphonate of the layer 16, such as ibandronate, may also be mixed into the layers 14.

As indicated above, the first bisphosphonate layers 14a, 14b may be immobilized onto the protein layers 12a–f. Preferably, the first layers 14a, 14b are bisphosphonates containing a chemically reactive group, such as pamidronate substance that may be covalently bound to cross-linked protein layers 12a–f. For instance, the amine group of a pamidronate molecule may be attached to an uppermost layer 12f after activation of protein with EDC/NHS.

Implantation trauma often results in bone resorption that negatively affects the mechanical fixation of the implant device. One feature of bisphosphonates is that they inhibit bone resorption and likely decrease inflammatory activity of monocytes and macrophages, thereby improving over time the fixation and integration of the implant device both when the drug is applied by local sudden treatment methods or by long-term systemic treatment. A localized surface dosage of about 120 ng/cm$^2$ is sufficient to increase fixation. A rapid mechanical fixation of the implant device 10 is important for the metallic prosthesis development, not only for patients with compromised bone healing capacity but also for normal and healthy patients. A faster mechanical fixation likely improves the functionality of a prosthesis due to an earlier and higher mechanical load uptake capacity. In parallel to this, it also decreases the thickness of the fibrous encapsulation and improves interfacial neo-vascularization. Early micromotion of the implant device is thus minimized, and the risk of late loosening reduced.

Preferably, the second bisphosphonate layer 16 is a chemically low- or non-reactive substance, such as ibandronate, that is applied to the protein layers 12 and the layers 14a, 14b by other binding mechanisms such as hydrophobic and van der Waals interactions. The bonding may also involve calcium ion ($Ca^{++}$)-bridging. In this way, it is not necessary that the second bisphosphonate layer 16 possess chemically reactive groups. The low- or non-reactive reactive bisphosphonate may be adsorbed or attached to immobilized pamidronate on or in a protein film so that a layer of about 6 Ångstroms is formed during an overnight incubation so that a total of at least three layers of bisphosphonate are present.

The fact that the loosely bound bisphosphonate layer 16 is easily released from the implant device 10 may have important advantages short time (up to 24 hours) after the implant device has been inserted. The insertion of implants into tissue often results in damage of the tissue matrix and disruption of the microcirculation in the immediate proximity of the implant. Matrix damage may, in case of bone, cause osteocyte apoptosis that may be implicated in osteoclast activation and remodelling, resulting in net bone resorption around the implant device. This likely leads to impairment of the implant fixation. The acute and rapid release of the second layer 16 of bisphosphonate may specifically and effectively inhibit osteoclast activity and reduce bone resorption. This is of particular importance during the first couple of days or longer after insertion of the implant device. Further, there is a possibility that bisphosphonates have direct stimulatory effects on bone forming cells. As indicated above, bisphosphonates reduce the osteoclast precursor (monocytes/macrophages) activity in soft tissue, thereby lowering the non-acute, implant-prolonged, phase of the inflammatory process. Prolonged inflammatory activity is suspected to be one of the main reasons of fibrosis in soft tissue. Surface delivery of bisphosphonates shortens the inflammatory activity giving a faster wound healing process around implants. Non-amino bisphosphonate substances may be particularly useful to reduce the inflammatory reaction. This will improve implant functions, such as lowering of the voltage threshold in pacemaker-leads that contact heart muscles, and improve measurement of various soft tissue and body fluid properties, i.e. in biosensors.

As indicated in FIG. 2, the total thickness of bisphosphonate layers 14a, 14b and 16 may be about 18 Ångstroms or more. A total thickness of the bisphosphonate layers of about 35–36 Ångstroms or more may be obtained where the surface 11 is roughened and the surface area increased. The bisphosphonate release mechanism may rely on a spontaneous desorption of non-covalently bound bisphosphonate and release of covalently bound ditto via hydrolytic and enzymatic cleavage of proteins. Approximately 30–50% of the bisphosphonate layer 16 may be desorbed during an overnight incubation in distilled water.

EXAMPLE

Stainless steel screws, with threads measuring 1.7 mm in diameter and 3 mm in length were used. Each screw had a hole defined in the head thereof so that it could be fastened with a hook suspended in a material testing machine. The screw specimens were cleaned for five minutes in acetone in an ultrasonic bath. The specimens were then etched during twenty minutes in 100% hydrofluoric acid (HF) and washed in a basic hydrogen peroxide solution at 80° C. for five minutes and finally rinsed in distilled water. Holes and asperities in the size range 0.1–100 micrometers were observed on the etched surface.

The screw specimens were put in a chamber with 0.2M 3-aminopropyltriethoxysilane $H_2N(CH_2)_3Si(OC_2H_5)_3$ (APTES from ABCR, Germany) and baked at 60° C. at 6 mbar for ten minutes. The temperature was then increased to 150° C. for one hour. The surfaces of the specimens were rinsed for two minutes in xylene (99% concentration, Merck, USA) in an ultrasonic bath. The surfaces were thereafter rinsed in xylene and stored in xylene no longer than one hour until the specimens were treated again. The so coated specimens were blown dry with flowing nitrogen and incubated for 30 minutes in freshly prepared 6% glutardialdehyde, $OHC(CH_2)_3CHO$, at room temperature in 0.2M Tris buffer, pH 9, to create a good environment for the reaction with aldehyde groups. The surfaces were then extensively rinsed and stored in the Tris buffer, pH 9.

Screws with ten layers of fibrinogen were prepared in the following way. The APTES and glutardialdehyde-coated specimens were incubated for thirty minutes in 1 mg/ml protein dissolved in phosphate buffered saline (PBS), pH 7.4. The specimen surfaces were thereafter extensively rinsed in PBS and incubated for thirty minutes in PBS at pH 5.5, containing 0.2M ethyl-dimethyl-aminopropylcarbodiimide (EDC, Sigma, USA). The specimen surfaces were again incubated for thirty minutes in a newly made 1-mg/ml protein solution in PBS, pH 5.5, thereafter rinsed in the PBS buffer and again incubated in the EDC/NHS solution. This procedure was repeated ten times to produce the ten-layer fibrinogen coating. Since the EDC/NHS solution is unstable at room conditions, new solutions were prepared every second hour.

Pamidronate disodium (AREDIA, 1 mg/ml in distilled water, Novartis, Sweden) was immobilized to the fibrinogen multiplayer using the above-described EDC/NHS coupling technique. An ibandronate solution (BONDRONATE, 50 mg/ml in distilled water, Roche, Switzerland) was adsorbed overnight on top of the pamidronate. The screw specimens were stored in the ibandronate solution for up to 24 hours until the specimens were inserted into rat tibia.

The thickness of the cross-linked fibrinogen layer was approximately 280 Ångstroms and the pamidronate layers about 12 Ångstroms. The more loosely attached ibandronate layer was about 6 Ångstroms thick. The total amount of immobilized bisphosphonate was approximately 120 ng/cm$^2$. The amine groups of the pamidronate molecules were attached to the uppermost fibrinogen layer after activation of the fibrinogen film with EDC/NHS. Ibandronate adsorbed or attached to the immobilized pamidronate and about a monolayer (6 Ångstroms) was formed during the overnight incubation.

The pamidronate/ibandronate-coated surfaces of the stainless steel implant devices showed a mean of 28% (p=0.0009) increased pullout force at failure compared to non-bisphosphonate coated control specimens, as shown in FIG. 3. The bone stiffness decreased by 8% compared to the control specimens although the change was not statistically significant. The pullout energy until failure increased by 90%, indicating drastically changed mechanical characteristics at the interface between the rat tibia and the bisphosphonate-coated specimen. This strongly indicates that the immobilized bisphosphonate layers 14a, 14b, 16 of the implant device 10 improved the metallic biomaterial fixation in bone.

While the present invention has been described in accordance with preferred compositions and embodiments, it is to be understood that certain substitutions and alterations may be made thereto without departing from the spirit and scope of the following claims.

The invention claimed is:

1. A method for coating an implant device, comprising:
   coating the implant device with a protein;
   covalently immobilizing a first substance having an amino group to the protein; and
   adsorbing a bisphosphonate substance to the first substance, the first substance being different from the bisphosphonate substance.

2. The method according to claim 1 wherein the immobilizing step comprises covalently linking a reactive group such as an amino group of bisphosphonate to the protein.

3. The method according to claim 1 wherein the adsorbing step comprises using a chemically non-reactive bisphosphonate.

4. The method according to claim 1 wherein the coating steps further comprises using a cross-linked protein.

5. The method according to claim 1 wherein the method further comprises etching a surface of the implant device.

6. The method according to claim 1 wherein the method further comprises creating a plurality of protein layers by cross-linking the protein layers with ethyl-dimethyl-aminopropylcarbodiimide (EDC) and hydroxy-succinimide (NHS).

7. The method according to claim 1 wherein the coating step further comprises immobilizing a first protein layer onto a surface of the implant device via an attachment of amino propyl triethoxy silane (APTES).

8. The method according to claim 7 wherein the coating steps further comprises using glutaraldehyde to chemically bind the APTES and glutaraldehyde to amino groups of the first protein layer.

9. An implant device, comprising:
   a multilayer of protein chemically bound to a surface of the implant device;
   a chemically immobilizable bisphosphonate layer covalently bound to the protein film; and
   a chemically non-reactive bisphosphonate layer non-covalently bound to the first bisphosphonate layer.

10. The implant device according to claim 9 wherein the second bisphosphonate layer is bound to the protein film only by non-covalent interactions.

* * * * *